United States Patent [19]

Masuda et al.

[11] Patent Number: 6,042,798

[45] Date of Patent: *Mar. 28, 2000

[54] METHOD OF DESULFURIZATION OF HYDROCARBONS

[75] Inventors: Masataka Masuda, Osaka; Osamu Okada, Osakasayama; Takeshi Tabata, Toyonaka; Yasuhiro Hirai, Matsubara; Hiroki Fujita, Osaka, all of Japan

[73] Assignee: Osaka Gas Company Limited, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/785,379

[22] Filed: Jan. 21, 1997

Related U.S. Application Data

[63] Continuation of application No. 08/531,831, Sep. 21, 1995, abandoned, which is a continuation of application No. 08/158,216, Nov. 29, 1993, abandoned.

[30] Foreign Application Priority Data

Nov. 28, 1992 [JP] Japan .................................... 4-341506

[51] Int. Cl.⁷ .............................. B01J 8/00; C10G 45/02; C07C 7/12
[52] U.S. Cl. ................................ 423/244.01; 423/244.06; 208/208 R; 208/246; 585/820; 585/823; 585/848; 585/850
[58] Field of Search ............................... 208/208 R, 246; 585/820, 823, 850, 852, 848; 423/244.07, 244.02, 244.06

[56] References Cited

U.S. PATENT DOCUMENTS

| | | | |
|---|---|---|---|
| 4,391,677 | 7/1983 | Harris et al. | 203/28 |
| 4,582,819 | 4/1986 | Miller et al. | 502/415 |
| 5,026,536 | 6/1991 | Shioiri et al. | 423/652 |
| 5,157,201 | 10/1992 | Norris | 585/820 |

FOREIGN PATENT DOCUMENTS

| | | |
|---|---|---|
| 0 324 071 | 7/1989 | European Pat. Off. . |
| 0324071 | 7/1989 | European Pat. Off. . |
| 0 398 251 | 11/1990 | European Pat. Off. . |
| 0398251A1 | 11/1990 | European Pat. Off. . |
| 0243052B1 | 1/1992 | European Pat. Off. . |
| 59-196829A | 8/1984 | Japan . |
| 59-196829 | 11/1984 | Japan . |
| 2-52041 | 2/1990 | Japan . |
| 1421731 | 9/1988 | U.S.S.R. . |
| 1011001 | 11/1965 | United Kingdom . |
| 1142339 | 2/1969 | United Kingdom . |
| 1153564 | 5/1969 | United Kingdom . |
| 1522389 | 8/1978 | United Kingdom . |

OTHER PUBLICATIONS

JP59196829 English language Abstract Nov. 1984.

Catalyst Handbook, Second Edition, Martyn V. Twigg, Chapter 4, Feedstock Purification, pp. 194 and 200, 1989.

Ullmann's Encyclopedia of Industrial Chemistry, Fifth, Completely Revised Edition, vol. A12: "Formamides to Hexamethylenediamine", Elvers et al. p. 189, 1989.

"Thermodynamics of sulfur chemisorption on metals. I. Alumina–supported nickel", J. Chem. Phys. 72(12), Jun. 15, 1980, pp. 6332–6337.

"Thermodynamics of Sulfur chemisorption on metals. II. Alumina–supported ruthenium", J. Chem. Phys. 74(10), May 15, 1981, pp. 5877–5830.

*Primary Examiner*—Walter D. Griffin
*Attorney, Agent, or Firm*—Finnegan, Henderson, Farabow, Garrett & Dunner, L.L.P.

[57] ABSTRACT

A method for the desulfurization of hydrocarbons by desulfurizing unsaturated hydrocarbons or hydrocarbon materials containing unsaturated hydrocarbons, in the presence or absence of hydrogen, using a copper-zinc desulfurizing agent prepared by the co-precipitation method. By this method, the sulfur content of the hydrocarbons can be reduced while suppressing hydrogenation of the unsaturated hydrocarbons.

16 Claims, No Drawings

METHOD OF DESULFURIZATION OF HYDROCARBONS

This application is a continuation of application Ser. No. 08/531,831, filed Sep. 21, 1995, now abandoned, which is a continuation of application Ser. No. 08/158,216, filed Nov. 29, 1993, abandoned.

TECHNICAL FIELD

The present invention relates to a desulfurization method of hydrocarbons. More particular, the invention relates to a desulfurization method capable of suppressing hydrogenation of unsaturated hydrocarbons or unsaturated hydrocarbons in hydrocarbon materials containing them as far as possible, and lowering the sulfur content in the hydrocarbon materials.

BACKGROUND ART

Hitherto, various gases and oils such as industrial gas, natural gas and petroleum fractions are presented for desulfurization process in order to eliminate adverse effects of sulfur contents contained therein, and are put in use after removal of sulfur contents. In certain processes using these hydrocarbons as materials, metal or noble metal catalysts are used as a catalyst of downstream, and these catalysts are generally susceptible to sulfur poisoning. Many metals are known to form surface sulfides on their surface even if sulfur of low concentration below the ppm order. For example, as unveiled by the studies of McCarty et al. (J. Chem. Phys. Vol. 72, No. 12, 6332, 1980, J. Chem. Phys. Vol. 74, No. 10, 5877, 1981), the sulfur adsorptivity of Ni and Ru is very strong, and therefore if the sulfur content in the material is about 0.1 ppm, the surface of Ni or Ru catalyst is covered almost entirely with sulfur in the equilibrium state (sulfur coverage 0.8 or more). As for other metals, it is reported that surface sulfides are likely to be formed and that sulfur poisoning occurs very easily. Therefore, to prevent sulfur poisoning of downstream catalysts and enhance the process economy, it is desired to lower the sulfur contents in materials as much as possible.

As the method for removing sulfur compounds contained in hydrocarbon materials, various methods have been known, and a general method is the hydrodesulfurization method of hydrogenating sulfur compounds to form hydrogen sulfide, and removing this hydrogen sulfide by using adsorbent such as zinc oxide. In this hydrodesulfurization method, however, when hydrogenating sulfur compounds into hydrogen sulfide, much hydrogen (for example, addition of hydrogen by about 0.05 to 0.1 to the material by molar ratio) is required, the unsaturated hydrocarbon itself, or the unsaturated hydrocarbon such as olefin contained in material hydrocarbon is also hydrogenated. Therefore it is not proper in the case of hydrocarbon which may be hydrogenated. For example, when refining ethylene, propylene, or other olefin compounds, or if not desired to decrease the olefin content in order to maintain the octane value in hydrocarbon material such as gasoline with high contents of unsaturated hydrocarbons such as olefin, it is not proper to employ the hydrodesulfurization method.

The Japanese Patent Unexamined Publication No. 196829/1984 and No. 52041/1990 disclose methods of desulfurization of olefinic hydrocarbons by using adsorbing desulfurizing agent of zinc oxide compound, but in these methods of desulfurization, although it is effective for sulfur compounds such as hydrogen sulfide, mercaptan and COS, the desulfurization effect is small in other sulfur compounds such as thiophene and sulfides.

Other method of desulfurization without hydrogenating olefin by hydrolytic desulfurization method is known, but the sulfur compounds that can be desulfurized are limited to carbon disulfide and carbonyl sulfide.

Besides, adsorption desulfurization by activated carbon or the like may be considered, but hydrocarbon contained in the hydrocarbon material is absorbed at the same time, almost all of the sites that should be adsorbed by the sulfur compound, in principle, cannot be utilized, and if attempted to keep a sufficient sulfur adsorption amount, a huge volume of activated carbon is required.

It is hence a primary object of the invention to present a method of desulfurization capable of desulfurizing at high degree, while suppressing hydrogenation of unsaturated hydrocarbon by solving the problems of the conventional methods of desulfurization.

SUMMARY OF THE INVENTION

The present inventors accumulated studies in order to solve the problems of the prior arts, and discovered that the sulfur content in hydrocarbon materials can be lowered by desulfurizing olefin and other unsaturated hydrocarbons or hydrocarbon materials containing them by using copper-zinc desulfurizing agents prepared by co-precipitation method; and further discovered that hydrogenation of unsaturated hydrocarbon can be suppressed as much as possible and that the sulfur content in the hydrocarbon materials can be remarkably lowered by desulfurizing by adding a small amount of hydrogen at this time, and hence completed the present invention.

More specifically, the method of desulfurization of the invention is characterized by desulfurizing unsaturated hydrocarbon or hydrocarbon containing unsaturated hydrocarbon by using copper-zinc desulfurizing agents prepared by co-precipitation method, and further adding hydrogen to the hydrocarbon material at this time.

DETAILED DESCRIPTION OF THE INVENTION

In the desulfurization method of the invention, using copper-zinc desulfurizing agent prepared by co-precipitation method as desulfurizing agent, unsaturated hydrocarbon or hydrocarbon material containing unsaturated hydrocarbon is brought into contact with the desulfurizing agent, in the presence or absence of hydrogen.

As the copper-zinc desulfurizing agent, it is not particularly limited as far as the desulfurizing agent prepared by co-precipitation method and containing at least copper (metal) and zinc oxide, and preferably Cu—Zn desulfurizing agent and Cu—Zn—Al desulfurizing agent prepared by the following methods may be used.

(1) Cu—Zn desulfurizing agent

An aqueous solution containing copper compound (such as copper nitrate and copper acetate) and zinc compound (such as zinc nitrate and zinc acetate) and an aqueous solution of an alkaline substance (such as sodium carbonate and potassium carbonate) are mixed to form precipitate (co-precipitation method). The formed precipitate is washed sufficiently with water, filtered, and dried. It is then calcined at about 270 to 400° C., and is once transformed into slurry by adding water, and then filtered and dried, and a mixture of copper oxide and zinc oxide is obtained. The ratio of copper oxide and zinc oxide is generally, by atomic ratio, copper:zinc=1: about 0.3 to 10, or preferably 1: about 0.5 to 3, or more preferably 1: about 1 to 2.3. If the zinc content is too small, sintering of copper cannot be prevented effectively, or if the zinc content is too much, to the contrary, the sufficient desulfurization performance as copper based desulfurizing agent cannot be exhibited. Consequently, thus obtained mixed oxide is subjected to hydrogen reduction. Hydrogen reduction is conducted by reducing the mixture at about 150 to 350° C. in the presence of hydrogen gas diluted with gas not responsible for reaction (such as nitrogen gas, argon gas, methane gas, etc.) so that the hydrogen content may be 6% or less, preferably about 0.5 to 4 vol. %. Thus obtained Cu—Zn desulfurizing agent may contain metals belonging to group VIII in the periodic table (such as Fe, Co, Ni, Ru, Rh, Pd, Os, Ir, Pt), group IB (such as Ag, Au), or group VIB (such as Cr, Mo, W), and more specifically oxides of these metals may be presented (such as iron oxide, cobalt oxide, nickel oxide, ruthenium oxide, palladium oxide, silver oxide, chromium oxide, molybdenum oxide, tungsten oxide). In this process, moreover, when calcining the precipitate or reducing the mixture in hydrogen, it is preferred to form into tablet, extrusion forming or other shape after adding additives as required.

(2) Cu—Zn—Al desulfurizing agent

An aqueous solution containing copper compound (such as copper nitrate, copper acetate), zinc compound (such as zinc nitrate, zinc acetate) and aluminum compound (such as aluminum hydroxide, aluminum nitrate, sodium aluminate) and an aqueous solution of alkaline substance (such as sodium carbonate, potassium carbonate) are mixed to form precipitate (co-precipitation method).

At this time, by adding aluminum compound to the solution of alkaline substance, this solution and the aqueous solution containing copper compound and zinc compound may be mixed to form precipitate. Successively, the formed precipitate is sufficiently washed with water, filtered, and dried. Next, it is calcined at about 270 to 400° C., and is once transformed into slurry by adding water, and filtered, and dried, thereby obtaining a mixture of copper oxide-zinc oxide-aluminum oxide. The ratio of copper oxide, zinc oxide and aluminum oxide is generally, by atomic ratio, copper:zinc:aluminum=1: about 0.3 to 10: about 0.05 to 2, or preferably 1: about 0.6 to 3: about 0.3 to 1. If the zinc content is too small, sintering of copper cannot be prevented effectively, or if the zinc content is excessive, on the other hand, the sufficient desulfurization performance as copper based desulfurizing agent cannot be exhibited. If the aluminum content is too small, the Cu—ZnO structure cannot be stabilized, or if the aluminum content is excessive, the desulfurization performance is lowered. Thus obtained mixed oxide is subjected to hydrogen reduction. Hydrogen reduction is conducted by reducing the mixture at about 150 to 350° C. in the presence of hydrogen gas diluted with gas not responsible for reaction (such as nitrogen gas, argon gas, methane gas, etc.) so that the hydrogen content may be 6% or less, preferably about 0.5 to 4 vol. %. Thus obtained Cu—Zn—Al desulfurizing agent may contain certain metals as other carrier components, for example, metals belonging to group VIII in the periodic table (such as Fe, Co, Ni, Ru, Rh, Pd, Os, Ir, Pt), group IB (such as Ag, Au), or group VIB (such as Cr, Mo, W), and more specifically oxides of these metals may be presented (such as iron oxide, cobalt oxide, nickel oxide, ruthenium oxide, palladium oxide, silver oxide, chromium oxide, molybdenum oxide, tungsten oxide). In this process, moreover, when calcining the precipitate or reducing the mixture in hydrogen, it is preferred to form into tablet, extrusion forming or other shape after adding additives as required.

Concerning the hydrogen reduction of mixed oxide in (1) and (2), since the copper has a low melting point and the particle size is increased by heat, and the surface area is likely to decrease, and the porous structure is delicately changed by excessive heat, and, as a result, the characteristic as the desulfurizing agent is greatly changed. In addition, hydrogen reduction of copper oxide is an exothermic reaction. Therefore, in the hydrogen reduction of mixed oxide, it is preferred to progress the hydrogen reduction of the mixed oxide in moderate conditions, and it is a preferred method to reduce while keeping the temperature around 150 to 350° C., in the presence of hydrogen gas diluted with gas not responsible for reaction. As the gas not responsible for reaction, inert gas such as nitrogen gas is preferably used.

The copper-zinc desulfurizing agent obtained in this method has a fine structure composed of aggregates of particles, and very tiny copper particles are uniformly dispersed on the surface of zinc oxide particles, and copper is in highly active state by chemical interaction with zinc oxide. In Cu—Zn—Al desulfurizing agent, aluminum oxide is distributed entirely, and sintering of copper particles and zinc oxide particles by heat is prevented, so that the highly active state is held. Therefore, when using such desulfurizing agents, the sulfur content in the hydrocarbon material can be securely lowered. In particular, with the Cu—Zn—Al desulfurizing agent, by the action of aluminum oxide, it is excellent in heat resistance, and lowering of strength and lowering of sulfur adsorption capacity at high temperature can be notably decreased, and the limitations of the usable temperature range may be alleviated.

On the other hand, Cu is often used in hydrogenation of olefin, but the hydrogenation activity is generally lower as compared with other metals. Schuit et al. presented the following sequence about hydrogenation activity of metal supported on silica on ethylene.

Rh>R u>Pd>Pt, Ni>Ir,Co>Fe>Cu

According to this sequence, Cu are generally shown to be low in the hydrogenation activity. Therefore, when using the copper-zinc desulfurizing agent obtained by the above method, decomposition and adsorption reactions of sulfur compounds dominate the hydrogenation reaction of unsaturated hydrocarbons, and it is hence possible to remove the sulfur compounds contained in the raw materials, while suppressing as much as possible the hydrogenation of unsaturated hydrocarbons.

In the method of desulfurization of the invention, the copper-zinc desulfurization agent prepared by the above method is used in a temperature range of 70 to 350° C. The temperature of desulfurization should be as high as possible from the viewpoint of acceleration of decomposition reaction rate of sulfur compounds, but if the temperature is too high, the copper components of the desulfurizing agent may induce sintering, and the surface area of the desulfurizing agent decreases. At the same time, hydrogenation of unsaturated hydrocarbons and side reactions may increased. Therefore, realistically, it is preferred to use at 100 to 200° C.

The method of desulfurization of the invention is generally effected by passing material hydrocarbon alone or material hydrocarbon and hydrogen, into the desulfurization tube filled with copper-zinc desulfurizing agent. The amount of hydrogen to be added is adjusted by the type and quantity of sulfur contained in the materials, strictly, but the actual content of sulfur is in the order of ppm, and hence it is desired to add hydrogen by 0.01% (vol. %, same hereinafter) or more, or preferably 0.1% or more. If the hydrogen amount is excessive, to the contrary, the amount of unsaturated hydrocarbons to be hydrogenated increases, and therefore it is desired to add hydrogen usually by about 4% or less (preferably about 2% or less). The filling amount of desulfurizing agent may be properly set depending on the sulfur content in the material hydrocarbon, desulfurization conditions of use, and others, but it may be usually set so that the GHSV may be about 200 to 4,000 liters/h, preferably 300 to 2,000 liters/h.

Hydrocarbon materials used in the invention are not particularly limited, and examples may include, among others, alkenes such as ethylene, propylene, butene, isobutylene, pentene, hexene, and heptene (olefin hydrocarbons), alkynes such as acetylene, methyl acetylene, and 1-butyne (acetylene hydrocarbons), other unsaturated hydrocarbons, and alkanes (paraffin hydrocarbons) and alicyclic hydrocarbons containing these unsaturated hydrocarbons. In particular, they may be preferably used in removal of sulfur compounds contained in naphtha or gasoline having high contents of ethylene, propylene, and butene, hexene, and unsaturated hydrocarbon.

To extend the life of copper-zinc desulfurizing agent, it is preferred to fill with zinc oxide adsorption desulfurizing agent prior to copper-zinc desulfurizing agent, and preliminarily remove the sulfur compounds that may be adsorbed by zinc oxide. According to this method, since the hydrogen sulfide or mercaptan contained in the hydrocarbon material can be removed by zinc oxide, the load of the copper-zinc desulfurizing agent is alleviated, and, as a result, the life is extended.

According to the invention, since the copper-zinc desulfurizing agent extremely excellent in desulfurization performance is used, the sulfur content in the unsaturated hydrocarbon or hydrocarbon material containing it may be reduced. At this time, by adding a small amount of hydrogen, the desulfurization performance is enhanced, and hydrogenation of unsaturated hydrocarbon is substantially suppressed, and the sulfur content in the hydrocarbon material is extremely lowered. Furthermore, since the hydrogenation reaction of unsaturated hydrocarbon generates a large amount of heat, and cooling device was needed in the conventional method, but in the method of the invention, the amount of addition of hydrogen is small, and hydrogenation reaction of unsaturated hydrocarbons is suppressed, so that the heat generation is small, and any particular device is not necessary.

Therefore, in the case of reaction of unsaturated hydrocarbon or hydrocarbon material containing it by using catalyst susceptible to sulfur poisoning, by desulfurizing the material according to the method of the invention, sulfur poisoning of catalyst can be prevented, and adverse effects of sulfur can be eliminated. When using unsaturated hydrocarbon or hydrocarbon material containing it as fuel, the SOx concentration in the combustion exhaust gas can be decreased.

EXAMPLES

The invention is more specifically described below by referring to Examples and Comparative Examples, but the invention is not limited to these embodiments alone.

Example 1

A mixed aqueous solution containing copper nitrate, zinc nitrate and aluminum hydroxide at a molar ratio of 1:1:0.3 was dropped into an aqueous solution of sodium carbonate kept at about 60° C. while stirring to form precipitate. The precipitate was sufficiently washed with water, filtered, and dried. Consequently, it was calcined at about 280° C., and was once transformed into slurry by adding water, and filtered, and dried, and a mixture of copper oxide-zinc oxide-aluminum oxide of 8×14 mesh was obtained.

In a desulfurization tube (desulfurization layer length 30 cm) filled with about 150 cc of the mixture, nitrogen gas containing 1 vol. % of hydrogen was passed to reduce at temperature of 200° C., and 150 liters/h of ethylene gas containing 11(mg-S/m$^3$) of thiophene (GHSV=1000 h$^{-1}$), and 1.5 liters/h of hydrogen were passed through the desulfurization tube, and desulfurization was conducted at temperature of 200° C. and pressure of 5 kg/cm$^2$-G.

As a result, nearly 99% of the refined gas obtained finally was ethylene, and the sulfur compound content was a level of 0.1 ppm or less in average throughout operation for 240 hours.

Example 2

In a desulfurization tube (desulfurization layer length 30 cm) filled with 150 cc of the mixture of copper oxide-zinc oxide-aluminum oxide obtained in the same manufacturing method as in Example 1, nitrogen gas containing 1 vol. % of hydrogen was passed to reduce at temperature of 200° C., and 150 liters/h of ethylene gas containing 11(mg-S/m$^3$) of thiophene (GHSV=1000 h$^{-1}$), and 1.5 liters/h of hydrogen were passed through the desulfurization tube, and desulfurization was conducted at temperature of 100° C. and pressure of 5 kg/cm$^2$-G.

As a result, nearly 99% of the refined gas obtained finally was ethylene, and the sulfur compound content was a level of 0.1 ppm or less in average throughout operation for 300 hours.

Example 3

In a desulfurization tube (desulfurization layer length 30 cm) filled with 150 cc of the mixture of copper oxide-zinc oxide-aluminum oxide obtained in the same manufacturing method as in Example 1, nitrogen gas containing 1 vol. % of hydrogen was passed to reduce at temperature of 200° C., and 150 liters/h of ethylene gas containing 11(mg-S/m$^3$) of thiophene (GHSV=1000 h$^{-1}$), and 1.5 liters/h of hydrogen were passed through the desulfurization tube, and desulfurization was conducted at temperature of 70° C. and pressure of 5 kg/cm$^2$-G.

As a result, nearly 99% of the refined gas obtained finally was ethylene, and the sulfur compound content was a level of 0.1 ppm or less in average throughout operation for 240 hours.

Example 4

In a desulfurization tube (desulfurization layer length 30 cm) filled with 150 cc of the mixture of copper oxide-zinc oxide-aluminum oxide obtained in the same manufacturing method as in Example 1, nitrogen gas containing 1 vol. % of hydrogen was passed to reduce at temperature of 200° C., and 150 liters/h of ethylene gas containing 11(mg-S/m$^3$) of thiophene (GHSV=1000 h$^{-1}$), and 1.5 liters/h of hydrogen were passed through the desulfurization tube, and desulfurization was conducted at temperature of 100° C. and pressure of 8 kg/cm$^2$-G.

As a result, nearly 99% of the refined gas obtained finally was ethylene, and the sulfur compound content was a level of 0.1 ppm or less in average throughout operation for 360 hours.

Comparative Example 1

A reaction tube same as in Example 1 was filled with Ni—Mo hydrodesulfurization catalyst and ZnO adsorption desulfurizing agent, and 150 liters/h of ethylene gas containing 11(mg-S/m$^3$) of thiophene (GHSV=1000 h$^{-1}$), and 1.5 liters/h of hydrogen were passed through the desulfurization tube to perform hydrogenolysis in the conditions of temperature of 350° C. and pressure of 5 kg/cm$^2$-G, and desulfurization was conducted by contacting with ZnO adsorption desulfurization agent.

As a result, in about 3 hours, 0.1 ppm of thiophene was detected in the refined gas at the outlet of the reaction tube. Thereafter, elevation of thiophene concentration was noted.

Comparative Example 2

A reaction tube same as in Example 1 was filled with Ni—Mo hydrodesulfurization catalyst and ZnO adsorption desulfurizing agent, and 150 liters/h of ethylene gas containing 11(mg-S/m$^3$) of thiophene (GHSV=1000 h$^{-1}$), and 15 liters/h of hydrogen were passed through the desulfurization tube to perform hydrogenolysis in the conditions of temperature of 350° C. and pressure of 5 kg/cm$^2$-G, and desulfurization was conducted by contacting with ZnO adsorption desulfurization agent.

As a result, about 10% of the ethylene in the refined ethylene gas was hydrogenated to ethane.

Comparative Example 3

A reaction tube same as in Example 1 was filled with Ni—Mo hydrodesulfurization catalyst and ZnO adsorption desulfurizing agent, and 150 liters/h of ethylene gas containing 11(mg-S/m$^3$) of thiophene (GHSV=1000 h$^{-1}$), and 1.5 liters/h of hydrogen were passed through the desulfurization tube to perform hydrogenolysis in the conditions of temperature of 200° C. and pressure of 5 kg/cm$^2$-G, and desulfurization was conducted by contacting with ZnO adsorption desulfurization agent.

As a result, from right after start of experiment, more than 0.1 ppm of thiophene was detected in the refined gas at the outlet of the reaction tube. Thereafter, elevation of thiophene concentration was noted.

Example 5

A mixed aqueous solution containing copper nitrate and zinc nitrate at a molar ratio of 1:1 was dropped into an aqueous solution of sodium carbonate kept at about 60° C. while stirring to form precipitate. The precipitate was sufficiently washed with water, filtered, and dried. Consequently, it was calcined at about 280° C., and was once transformed into slurry by adding water, and filtered, and dried, and a mixture of copper oxide-zinc oxide of 8×14 mesh was obtained.

In a desulfurization tube (desulfurization layer length 30 cm) filled with about 150 cc of the mixture, nitrogen gas containing 1 vol. % of hydrogen was passed to reduce at temperature of 200° C., and 150 liters/h of ethylene gas containing 11(mg-S/m$^3$) of thiophene (GHSV=1000 h$^{-1}$), and 1.5 liters/h of hydrogen were passed through the desulfurization tube, and desulfurization was conducted at temperature of 200° C. and pressure of 5 kg/cm$^2$-G.

As a result, nearly 99% of the refined gas obtained finally was ethylene, and the sulfur compound content was at a level of 0.1 ppm or less in average throughout operation for 240 hours.

Example 6

In a desulfurization tube (desulfurization layer length 30 cm) filled with 150 cc of the mixture of copper oxide-zinc oxide-aluminum oxide obtained in the same manufacturing method as in Example 1, nitrogen gas containing 1 vol. % of hydrogen was passed to reduce at temperature of 200° C., and 150 liters/h of propylene gas containing 11(mg-S/m$^3$) of thiophene (GHSV=1000 h$^{-1}$), and 1.5 liters/h of hydrogen were passed through the desulfurization tube, and desulfurization was conducted at temperature of 100° C. and pressure of 5 kg/cm$^2$-G.

As a result, nearly 99% of the refined gas obtained finally was propylene, and the sulfur compound content was a level of 0.1 ppm or less in average throughout operation for 300 hours.

Example 7

A mixed aqueous solution containing copper nitrate, zinc nitrate and nickel nitrate at a molar ratio of 45:50:5 was dropped into an aqueous solution of sodium carbonate kept at about 60° C. while stirring to form precipitate. The precipitate was sufficiently washed with water, filter, and dried. It was calcined at about 280° C., and was once ground and formed, and crushed and screened into size of 1 to 2 mm, and a mixture of copper oxide-zinc oxide-nickel oxide was obtained.

In a desulfurization tube filled with about 3 cc of the mixture (10 mm in tube diameter, desulfurization layer length 4 cm), nitrogen gas containing 2 vol. % of hydrogen was passed to reduce at temperature of 200° C., and 12 liters/h of ethylene-nitrogen mixed gas (ethylene 20 vol. %, nitrogen 80 vol. %) containing 3(mg-S/m$^3$) of thiophene (GHSV=4000 h$^{-1}$) and 0.24 liters/h of hydrogen were passed through the desulfurization tube, and desulfurization was conducted in the conditions of temperature of 100° C. and pressure of 0.02 kg/cm$^3$-G.

As a result, nearly 20% of the refined gas obtained finally was ethylene, and the sulfur compound contents remained at a level under an average of 0.1 ppm throughout the operation for 60 hours.

Example 8

Using copper nitrate, zinc nitrate and palladium nitrate, a mixture of copper oxide-zinc oxide-palladium oxide was obtained in the same process as in Example 7.

Successively, using about 3 cc of the mixture, hydrogen reduction and desulfurization test were conducted in the same manner as in Example 7.

As a result, nearly 20% of the refined gas obtained finally was ethylene, and the sulfur compound contents remained at a level under an average of 0.1 ppm throughout the operation for 30 hours.

Example 9

Using copper nitrate, zinc nitrate and cobalt nitrate, a mixture of copper oxide-zinc oxide-cobalt oxide was obtained in the same process as in Example 7.

Successively, using about 3 cc of the mixture, hydrogen reduction and desulfurization test were conducted in the same manner as in Example 7.

As a result, nearly 20% of the refined gas obtained finally was ethylene, and the sulfur compound contents remained at a level under an average of 0.1 ppm throughout the operation for 36 hours.

Example 10

Using copper nitrate, zinc nitrate and iron nitrate, a mixture of copper oxide-zinc oxide-iron oxide was obtained in the same process as in Example 7.

Successively, using about 3 cc of the mixture, hydrogen reduction and desulfurization test were conducted in the same manner as in Example 7.

As a result, nearly 20% of the refined gas obtained finally was ethylene, and the sulfur compound contents remained at a level under an average of 0.1 ppm throughout the operation for 30 hours.

Example 11

Using copper nitrate, zinc nitrate and ruthenium chloride, a mixture of copper oxide-zinc oxide-ruthenium oxide was obtained in the same process as in Example 7.

Successively, using about 3 cc of the mixture, hydrogen reduction and desulfurization test were conducted in the same manner as in Example 7.

As a result, nearly 20% of the refined gas obtained finally was ethylene, and the sulfur compound contents remained at a level under an average of 0.1 ppm throughout the operation for 24 hours.

Example 12

Using copper nitrate, zinc nitrate and silver nitrate, a mixture of copper oxide-zinc oxide-silver oxide was obtained in the same process as in Example 7.

Successively, using about 3 cc of the mixture, hydrogen reduction and desulfurization test were conducted in the same manner as in Example 7.

As a result, nearly 20% of the refined gas obtained finally was ethylene, and the sulfur compound contents remained at a level under an average of 0.1 ppm throughout the operation for 42 hours.

Example 13

Using copper nitrate, zinc nitrate and ammonium paramolybdenate, a mixture of copper oxide-zinc oxide-molybdenum oxide was obtained in the same process as in Example 7.

Successively, using about 3 cc of the mixture, hydrogen reduction and desulfurization test were conducted in the same manner as in Example 7.

As a result, nearly 20% of the refined gas obtained finally was ethylene, and the sulfur compound contents remained at a level under an average of 0.1 ppm throughout the operation for 30 hours.

Example 14

Using copper nitrate, zinc nitrate and ammonium tungstenate, a mixture of copper oxide-zinc oxide-tungsten oxide was obtained in the same process as in Example 7.

Successively, using about 3 cc of the mixture, hydrogen reduction and desulfurization test were conducted in the same manner as in Example 7.

As a result, nearly 20% of the refined gas obtained finally was ethylene, and the sulfur compound contents remained at a level under an average of 0.1 ppm throughout the operation for 36 hours.

Example 15

A mixed aqueous solution containing copper nitrate and zinc nitrate at a molar ratio of 1:1 was dropped into an aqueous solution of sodium carbonate kept at about 60° C. while stirring to form precipitate. The precipitate was sufficiently washed with water, filtered, and dried. Consequently, it was calcined at about 280° C., and was once ground and formed, and crushed and screened to obtain a mixture of copper oxide-zinc oxide in a size of 1 to 2 mm.

In a desulfurization tube (tube diameter 10 mm, desulfurization layer length about 4 cm) filled with about 3 cc of the mixture, nitrogen gas containing 2 vol. % of hydrogen was passed to reduce at temperature of 200° C., and the desulfurization test was conducted in the same condition as in Example 7.

As a result, nearly 20% of the refined gas obtained finally was ethylene, and the sulfur compound content was at level of 0.1 ppm or less in average throughout operation for 42 hours.

Example 16

In a desulfurization tube (tube diameter 10 mm, desulfurization layer length about 4 cm) filled with about 3 cc of the mixture of copper oxide-zinc oxide prepared in the same manufacturing method as in Example 15, nitrogen gas containing 2 vol. % of hydrogen was passed to reduce at 200° C., and the desulfurization test was conducted in the same condition as in Example 7. However, hydrogen was not added.

As a result, nearly 20% of the refined gas obtained finally was ethylene, and the sulfur compound content was at level of 0.1 ppm or less in average throughout operation for 10 hours.

Example 17

In a desulfurization tube (tube diameter 10 mm, desulfurization layer length about 4 cm) filled with about 3 cc of the mixture of copper oxide-zinc oxide prepared in the same manufacturing method as in Example 15, nitrogen gas containing 2 vol. % of hydrogen was passed to reduce at 200° C., and the desulfurization test was conducted in the same condition as in Example 7. However, the amount of addition of hydrogen was 4 vol. % of the total gas volume.

As a result, nearly 15% of the refined gas obtained finally was ethylene, and the sulfur compound content was at level of 0.1 ppm or less in average throughout operation for 54 hours.

Comparative Example 4

In a desulfurization tube (tube diameter 10 mm, desulfurization layer length about 4 cm) filled with about 3 cc of the mixture of copper oxide-zinc oxide prepared in the same manufacturing method as in Example 15, nitrogen gas containing 2 vol. % of hydrogen was passed to reduce at 200° C., and the desulfurization test was conducted in the same condition as in Example 7. However, the amount of addition of hydrogen was 20 vol. % of the total gas volume.

As a result, in the refined gas obtained finally, ethylene was not contained from right after start of the test.

Comparative Example 5

A mixed aqueous solution containing zinc nitrate and nickel nitrate at a molar ratio of 1:1 was dropped into an aqueous solution of sodium carbonate kept at about 60° C. while stirring to form precipitate. The precipitate was sufficiently washed with water, filtered, and dried. It was then calcined at about 280° C., and once ground, and formed, then crushed and screen into a size of 1 to 2 mm, and a mixture of zinc oxide-nickel oxide was obtained.

Using about 3 cc of the mixture, hydrogen reduction and desulfurization test were conducted in the same manner as in Example 7.

As a result, in about 15 minutes after start of experiment, 1.6 ppm of thiophene was detected in the refined gas at the outlet of the reaction tube, and thereafter elevation of thiophene concentration was noted.

Comparative Example 6

Using zinc nitrate and cobalt nitrate, a mixture of zinc oxide-cobalt oxide was obtained in the same process as in Comparative Example 5.

Using about 3 cc of the mixture, hydrogen reduction and desulfurization test were conducted in the same manner as in Example 7.

As a result, in about 15 minutes after start of experiment, 1.3 ppm of thlophene was detected in the refined gas at the outlet of the reaction tube, and thereafter elevation of thiophene concentration was noted.

Comparative Example 7

Using zinc nitrate and Iron nitrate, a mixture of zinc oxide-iron oxide was obtained in the same process as in Comparative Example 5.

Using about 3 cc of the mixture, hydrogen reduction and desulfurization test were conducted in the same manner as in Example 7.

As a result, in about 15 minutes after start of experiment, 1.9 ppm of thiophene was detected in the refined gas at the outlet of the reaction tube, and thereafter elevation of thiophene concentration was noted.

What is claimed is:

1. A method for the desulfurization of a gas comprising unsaturated hydrocarbons in an amount greater than 20 vol. % comprising desulfurizing said gas in the presence of from about 0.01 to 4 vol. % of hydrogen by contacting said gas with a copper-zinc desulfurizing agent prepared by a co-precipitation method.

2. The method for the desulfurization of gas according to claim 1, wherein the copper-zinc desulfurizing agent is a Cu—Zn desulfurizing agent obtained by hydrogen reduction of a mixture of copper oxide and zinc oxide, which mixture has been prepared by the co-precipitation method using a copper compound and a zinc compound, at about 150 to 350° C. in the presence of an inert gas having a hydrogen content of 6 vol. % or less.

3. The method for the desulfurization of gas according to claim 1, wherein the copper-zinc desulfurizing agent is a Cu—Zn—Al desulfurizing agent obtained by hydrogen reduction of a mixture of copper oxide, zinc oxide and aluminum oxide, which mixture has been prepared by the co-precipitation method using a copper compound, a zinc compound, and an aluminum compound, at about 150 to 350° C. in the presence of an inert gas having a hydrogen content of 6 vol. % or less.

4. The method for the desulfurization of gas according to claim 2, wherein the hydrogen content of the inert gas is from 0.5 to 4 vol. %.

5. The method for the desulfurization of gas according to claim 4, wherein the atomic ratio of copper to zinc in the copper oxide-zinc oxide mixture is from about 1 to 0.3 to about 1 to 10.

6. The method for the desulfurization of gas according to claim 2, wherein the Cu—Zn desulfurizing agent also contains a metal belonging to group VIII, group IB or group VIB of the periodic table.

7. The method for the desulfurization of gas according to claim 3, wherein the hydrogen content of the inert gas is from 0.5 to 4 vol. %.

8. The method for the desulfurization of gas according to claim 3, wherein the hydrogen content of the inert gas is from 0.5 to 4 vol. %.

9. The method for the desulfurization of gas according to claim 8, wherein the atomic ratio of copper, zinc and aluminum in the copper oxide-zinc oxide-aluminum oxide mixture is 1: about 0.3 to 10: about 0.05 to 2.

10. The method for the desulfurization of gas according to claim 3, wherein the Cu—Zn—Al desulfurizing agent also contains a metal belonging to group VIII, group IB or group VIB of the periodic table.

11. The method for the desulfurization of gas according to claim 10, wherein the hydrogen content of the inert gas is from 0.5 to 4 vol. %.

12. The method for the desulfurization of gas according to claim 1, 5, 7, 9 or 11, wherein the unsaturated hydrocarbon is ethylene, propylene, butene, hexene, or naphtha or gasoline containing unsaturated hydrocarbons.

13. The method for the desulfurization of gas according to claim 1, wherein the hydrogen content during desulfurization is from about 0.1 to 2 volume %.

14. The method for the desulfurization of gas according to claim 1, wherein the hydrocarbons are selected from the group consisting of alkenes, alkynes, and alkanes and alicyclic hydrocarbons containing unsaturated hydrocarbons.

15. The method for the desulfurization of gas according to claim 1, wherein the hydrocarbon is a hydrocarbon material containing unsaturated hydrocarbons and is gasoline.

16. The method for the desulfurization of gas according to claim 15, wherein the gasoline contains unsaturated hydrocarbons selected from the group consisting of ethylene, propylene, butene, and hexene.

* * * * *

UNITED STATES PATENT AND TRADEMARK OFFICE
CERTIFICATE OF CORRECTION

PATENT NO.    : 6,042,798
DATED         : March 28, 2000
INVENTORS     : Masataka MASUDA et al.

It is certified that error appears in the above-identified patent and that said Letters Patent is hereby corrected as shown below:

In Claim 7, column 12, line 16, "claim 3" should read --claim 6--.

Signed and Sealed this

Twentieth Day of March, 2001

*Attest:*

NICHOLAS P. GODICI

*Attesting Officer*  *Acting Director of the United States Patent and Trademark Office*